United States Patent [19]

Foldager et al.

[11] Patent Number: 5,068,109

[45] Date of Patent: Nov. 26, 1991

[54] ANTACID COMPOSITION

[75] Inventors: Jorgen Foldager, Snekkersten; Helle Toftkj r, N rum; Kim Kjorn s, V rlose, all of Denmark

[73] Assignee: Farma Food A/S, Glostrup, Denmark

[21] Appl. No.: 424,222

[22] PCT Filed: Apr. 6, 1988

[86] PCT No.: PCT/DK88/00062

§ 371 Date: Dec. 5, 1989

§ 102(e) Date: Dec. 5, 1989

[87] PCT Pub. No.: WO88/07862

PCT Pub. Date: Oct. 20, 1988

[30] Foreign Application Priority Data

Apr. 8, 1987 [DK] Denmark ............... 1796/87

[51] Int. Cl.[5] ............... A61K 9/28
[52] U.S. Cl. ............... 424/441; 514/819; 514/820
[58] Field of Search ............... 424/441; 514/819, 820

[56] References Cited

U.S. PATENT DOCUMENTS

| 2,836,540 | 5/1958 | Hardt ............... 424/464 |
| 3,474,086 | 10/1969 | Larde et al. ............... 260/209.5 |
| 4,056,566 | 11/1977 | Sakakibara et al. ............... 426/577 |
| 4,140,760 | 2/1979 | Withington ............... 424/81 |
| 4,167,558 | 9/1979 | Sheth et al. ............... 424/464 |
| 4,199,560 | 4/1980 | Gyarmati et al. ............... 424/489 |
| 4,315,918 | 2/1982 | Gayst et al. ............... 260/112 |

FOREIGN PATENT DOCUMENTS

| 2306706 | 4/1976 | France . |
| 8500652 | 4/1985 | PCT Int'l Appl. . |
| 8504806 | 11/1985 | PCT Int'l Appl. . |
| 1206870 | 9/1970 | United Kingdom . |

OTHER PUBLICATIONS

The United States Pharmacopeia, 21st Revision, p. 790.
May et al., International Journal of Pharmaceutics, 19 (1984), 169–176.
Washington et al., International Journal of Pharmaceutics, 39 (1987), 163–171.
Flourie et al., The American Journal of Clinical Nutrition, 42, Sep. 1985, 495–503.
Feldman et al., Gastroenterology 1984:87:895–902.
Mulmud et al., J. Nucl. Med. 20, (1979), 1023–1028.
Knight et al., Journal of Nuclear Medicine 27 (1986), 1011–1012.
Flourie et al., Gut, 25 (1984), 936–941.
Leeds et al., The Lancet, May 16, 1981, 1075–1078.
Stanciu et al., Rev. Med. Clin. Soc. Med. Nat. Jasi (1985), 89(2)233–6.
Holt et al., The Lancet i; 1981; pp. 636–639.
Ralphs et al., Gut 19, 1978, 986–7A (abstract).

*Primary Examiner*—Thurman K. Page
*Assistant Examiner*—D. Gabrielle Phelan
*Attorney, Agent, or Firm*—Birch, Stewart, Kolasch & Birch

[57] ABSTRACT

The present invention relates to an antacid composition with floating properties, and a method of treating or alleviating upper gastrointestinal dyspeptic disorders.

23 Claims, No Drawings

ANTACID COMPOSITION

TECHNICAL BACKGROUND

Upper abdominal dyspepsia is symptomatic of a variety of diseases such as ulcers, biliary conditions, pancreatitis and gastrooesophageal reflux. However, the symptoms (heartburn, regurgitation and epigastric pain) often associated with such conditions may also occur without apparently being attributable to any specific clinical conditions observed by X-ray or endoscopic analyses.

Thus, the symptoms are very common, at least once in a while, even among otherwise healthy individuals. It is estimated that about 50–60% of the adult population in the United States suffer from one form or another of acute upper gastrointestinal distress. The short-term or prolonged use of antacids is therefore widespread.

The antacid effect of most of the antacid compositions currently in use resides in their ability to neutralize gastric acids, resulting in an increased pH of the gastric contents. The acid neutralizing effect of such conventional antacids is known to be brief in vivo, which is ascribable to two principal causes: the normal gastric emptying rate which causes the composition to be transferred to the intestines before its acid neutralizing and buffering capacities have been exhausted, and "acid rebound" or increased acid secretion induced by increased release of gastrin from the so-called G cells of the antrum which are pH sensitive, the increased production of gastrin occurring at a pH of the gastric contents of about 4–5 or more. For these reasons, the acidity of the gastric contents will usually have reached its normal level 1–2 hours after ingestion of the antacid so that a dosage regimen involving the ingestion of repeated antacid dosages may be required, in particular for the long-term treatment of gastric conditions such as ulcers, rather than for short-term relief of dyspepsia.

The currently employed antacids usually contain one or more alkali metal or alkaline earth metal salts, aluminum salts or, less usually, bismuth salts as acid neutralizing agents. The most commonly employed mineral salts are sodium bicarbonate, calcium carbonate, aluminum salts or magnesium salts.

Sodium bicarbonate is known as a potent, effective and rapid-acting antacid which, however, only exhibits a short-term effect. It is a systemic antacid which is not recommended for prolonged use or in large doses as systemic absorption of the sodium ion in large quantities may cause alkalosis which is characterized by elevated levels of carbon dioxide and an increased pH in the plasma. Symptoms of alkalosis include headache, mental confusion and anorexia.

Calcium carbonate which is a non-systemic gastric antacid is known to cause rapid, prolonged and effective neutralization of gastric acid, but is not recommended as an antacid, primarily because of its "acid rebound" effect. Studies have shown that oral administration of an isotonic calcium chloride solution results in increased gastric acid secretion both in healthy individuals and, particularly, in ulcer patients (50–75%). In another study, free calcium in the stomach has been found to release gastrin which in turn, as described above, induces the formation of gastric acid. Apart from acid rebound, it may cause hypercalcaemia and constipation.

The most commonly employed aluminum salts are the hydroxide, carbonate or phosphate, primarily the hydroxide. Its acid neutralizing capacity is lower than that of other conventional antacids, and it may cause constipation. Aluminum salts are therefore often combined with magnesium salts, such as the oxide, hydroxide, carbonate and trisilicate, which have a higher acid neutralizing capacity than the aluminum salts, but which may also cause diarrhoea. In combination preparations, the two components are balanced to offset the effect of either on gastrointestinal functions. A combination of aluminum and magnesium hydroxide gels is present in many commercial antacids. Recently, aluminum has become suspected of contributing to the development of presenile dementia (Alzheimer's disease) for which reason its use as an antacid should perhaps be discouraged.

Thus, the use of the various alkaline salts discussed above is associated with several drawbacks in the form of a number of adverse effects of major or minor severity. These adverse effects are of greater importance in case of long-term treatment involving a high antacid dosage. In recent years other approaches to gastrointestinal diseases have been attempted, which have primarily been concerned with reducing acid secretion. Agents responsible for a reduction of acid secretion in the stomach comprise anticholinergics and $H_2$-receptor antagonists. Such agents, however, suffer from the serious disadvantage of having serious adverse effects in larger doses as well as being available on prescription only (which is a drawback since antacids are often used for short-term relief of dyspeptic symptoms so that reliable and safe antacid preparations should preferably be available as over-the-counter products).

It is generally recognized that the efficacy of an antacid should be evaluated according to the following parameters: the level of acid neutralizing capacity, the period of latency before the acid neutralizing effect sets in, i.e. before the pH is increased to 3, the highest pH measured and the duration of the period during which the pH is in the range of 3–5 (it is desirable that this period should be as long as possible). Although most of the antacids mentioned above show a high score when tested according to these parameters in vitro, their in vivo performance is less convincing due to the acid rebound and gastric emptying effects described above.

Therefore, there is a need for a safe, reliable antacid composition which exhibits the above-mentioned desirable properties of a high acid neutralizing capacity and prolonged effect without being subject to the acid rebound effect common to several of the known antacids, and which has few, if any, adverse effects.

SUMMARY OF THE INVENTION

Accordingly, the present invention relates to an antacid composition which comprises
  a) a substance which is soluble in water at a neutral or alkaline pH, but which is capable of forming a cohesive gel at an acid pH,
  b) a substance which is capable of acting as a buffer and which is capable of being captured in the gel structure formed by substance a) at an acid pH, and
  c) one or more acid neutralizing agents capable of being trapped in the gel structure formed by substance a) at an acid pH, at least one of which causes the gel to foam when contacted with an acid,
the composition being formulated so that substance a) is dissolved before ingestion of the composition and having raft-forming properties in a gastric environment.

In the present context, the term "raft-forming properties" should be understood to mean that in the gastric environment, the composition of the invention will form a highly viscous cohesive gel which floats on top of the gastric contents due to a lower bulk density than that of gastric fluid. Thus, the product of the invention will act as a barrier between the oesophagus and the gastric fluid, thereby preventing the acid gastric contents from being refluxed into the oesophagus. Another advantage of the raft-forming effect is that the acidity of the gastric fluid will not be reduced to so critical a level after ingestion of the composition as to result in a pH level at the antrum which would bring about release of gastrin from the pH sensitive G cells which in turn would induce increased acid secretion. A further advantage of the composition of the invention is that the acid neutralizing agent or agents c) are contained in the gel structure of substance a) and are therefore not emptied from the stomach at the same rapid rate observed with conventional antacid compositions where the acid neutralizing agent will be emptied from the stomach at such a rate that the acid neutralizing effect will not have been exhausted. Apart from this, the buffer incorporated in the composition of the invention will contribute to prolongating the acid neutralizing effect.

Antacid compositions which contain a gel-forming agent and an acid neutralizing agent are known (cf. N. Washington et al., *Int. J. Pharm.* 27, 1985, pp. 279–286 and N. Washington et al., *Int. J. Pharm.* 28, 1986, pp. 139–143). The gel-forming agent in these known compositions is alginic acid, and they further contain sodium bicarbonate and usually at least one other acid neutralizing agent as well. When ingested, the sodium alginate forms a foaming alginate gel containing the other acid neutralizing agent or agents. This gel floats on top of the stomach contents and prevents refluxing of gastric fluid into the oesophagus. However, compositions of this type have been estimated to contain too low amounts of acid neutralizing agents to buffer gastric acid effectively, and contrary to the product of the present invention, they do not contain any buffer captured in the gel structure formed on contact with the acidic gastric fluid. In an in vitro experiment, the composition of the present invention was found to be superior to one commercial alginic acid containing antacid with respect to acid neutralizing capacity (cf. Example 5). There is also some indication of inadequate raft formation by these known antacids (Knight et al., *J. Nucl. Med.* 27, No. 6, 1986, pp. 1011–1012).

DETAILED DESCRIPTION OF THE INVENTION

Apart from forming a gel at an acid pH, substance a) should preferably also be one which on dissolution forms a viscous mucilage, for instance when dissolved in the mouth as a result of mastication, the mucilage coating the mucous membranes of the oesophagus and stomach, thereby protecting them from the inflammatory effects of gastric acids. The mucilage formed by substance a) should preferably have a low viscosity as more highly viscous substances tend to adhere rather strongly to the teeth and produce a dryness in the mouth which would give the composition an unpleasant feel in the mouth. For the present purposes, it is advantageous to use gel-forming substances a) selected from natural or synthetic polysaccharides and proteinaceous substances. Suitable polysaccharides which may be employed in the composition of the invention are selected from pectin, alginic acid, carrageenan, or a cellulose derivative such as carboxy methyl cellulose (in particular sodium carboxy methyl cellulose).

At present, a particularly favoured polysaccharide is pectin since, apart from having favourable gel-forming and mucosa-coating properties as defined above, it has bile acid and lipid binding properties. As bile acids are believed to influence the occurrence of gastrooesophageal disorders (gastritis) and ulcers, pectin-containing compositions of the invention are considered to constitute a particularly useful embodiment of the present invention. Particularly useful pectins for the present purpose are low-methoxylated pectins and amidated pectins. By low-methoxylated pectin is meant pectin with a degree of methoxylation of not more than 15%. Pectins with a degree of methoxylation of not more than 10%, preferably not more than 5%, are particularly preferred. Salts of such low-methoxylated pectins may also be employed such as alkaline metal salts, e.g. sodium or potassium salts.

Proteinaceous substances which may be incorporated in the composition of the invention as substance a) are advantageously selected from gelatin, milk protein such as casein or a caseinate or whey protein, an amino acid (such as glycine) or a salt thereof, or a vegetable protein such as a soy protein isolate.

The buffer substance b) which is captured in the gel structure formed by substance a) at an acid pH changes the gel characteristics in that it is dispersed in the gel structure, e.g. by agglomerating in the gel in an acid environment, i.e. on the surface of the gel. It is preferred to employ a buffer substance b) which, apart from the properties indicated above, is also capable of imparting a greater rigidity to the gel formed by substance a) at an acid pH so that it disintegrates less rapidly under gastric conditions. If, for instance, a polysaccharide is used as the gel-forming substance a), the polysaccharide chains will enclose colloidal particles of the buffer substance b) and prevent agglomeration or coagulation thereof except on the gel surface. Without wishing to be limited to any theory, it is believed that the firmer gel structure results from enclosure of the colloidal particles of the buffer substance b) by the polysaccharide chains. The polysaccharide molecules are thereby pressed more closely together because of the presence of the colloidal particles taking up space which would otherwise be occupied by the polysaccharide chains (the so-called "excluded volumes" phenomenon).

Substances which have been found to exhibit excellent gel improving and buffer properties are primarily proteinaceous substances. The term "proteinaceous substances" is understood to mean substances comprising or consisting of proteins, peptides or amino acids. Examples of suitable substances are casein or a caseinate, such as sodium, potassium or ammonium caseinate, milk powder, gelatin, a vegetable protein such as a soy protein isolate, or an amino acid (such as glycine) or a salt thereof. It should, however, be understood that when the substance employed as substance a) is one of these proteinaceous substances, substance b) is not identical to substance a).

The currently most preferred buffer substances b) are casein, caseinates and milk powder (which of course contains either or both of these) as milk proteins are known to possess a high buffering capacity resulting in a longer duration of the antacid effect of the acid neutralizing agent. Furthermore, milk proteins form colloidal particles in the gel structure of substance a) under gastric conditions, whereby the gel is broken up as explained above. Milk powder has previously been used in itself as an antacid, but its beneficial effect in a composition of the present invention which also comprises a gel-forming agent and an acid neutralizing agent has not previously been recognized. When casein is employed as the buffer substance b) it is usually a casein acid-precipitated with, for instance, hydrochloric acid or lactic acid, or rennet casein.

If the gel is sufficiently rigid in itself, it is usually not necessary to improve its properties further. In such cases, a buffer may be selected primarily for its buffering capacity. One class of advantageous buffers to be employed when gel improving properties are not specifically required are the phosphates as their buffering capacity is conveniently high at about pH 5. Examples of useful phosphates are sodium, calcium, magnesium, ammonium, aluminum or potassium phosphate.

At least one of the acid neutralizing agents incorporated as substance c) in the composition of the invention is a substance which, on reacting with acid, causes foaming of the gel formed from substance a), due to the formation of gas bubbles by the reaction, which gas bubbles are trapped in the gel.

Substances which are capable of foaming gels when contacted with acids may be selected from some of the acid neutralizing agents used in conventional antacid compositions, e.g. pharmaceutically acceptable alkali metal, alkaline earth metal, aluminum, ammonium and bismuth salts. The alkali metal or alkaline earth metal may be selected from sodium, potassium, magnesium and calcium. Alkaline salts exhibiting the most advantageous foaming properties are the carbonate, bicarbonate or subcarbonate as these react with acid to form carbon dioxide.

An advantageous combination of acid neutralizing agents incorporated in the composition of the invention has been found to be potassium bicarbonate and magnesium subcarbonate, as the potassium bicarbonate forms carbon dioxide immediately on contact with gastric acid to foam the gel, while the magnesium subcarbonate reacts more slowly, so that the proportion of it which is not used immediately on ingestion of the composition is trapped within the foamed gel and is released slowly therefrom with formation of carbon dioxide, thereby also contributing to the continued floating to the gel.

The acid neutralizing agents indicated above may be combined with one or more other acid neutralizing agents, for instance oxides or hydroxides of an alkali metal or alkaline earth metal such as sodium, potassium, magnesium and calcium, or of aluminum. These will not contribute to the foaming of the gel, but will be trapped in the gel structure and be released slowly so that they are not emptied from the stomach before their acid neutralizing capacity is exhausted, which is a disadvantage of conventional antacids as explained above.

The antacid composition of the invention may be formulated as a liquid suspension of the components in a liquid which acts as a solvent for substance a), does not cause gelling of substance a) and does not react with the acid neutralizing agent or, for that matter, with any of the other components. A typical formulation of a liquid composition of the invention is disclosed in Example 4 below. It is, however, preferred to formulate the composition as a chewable tablet together with conventional tabletting excipients and diluents. Such a tablet must be chewed thoroughly before being swallowed in order to obtain solution of substance a) before ingestion as it would otherwise not be distributed properly over the gastric contents to form the required gel. In an alternative embodiment, the composition may be formulated as an effervescent tablet together with conventional excipients. The tablet is adapted to being disintegrated in a liquid before ingestion.

The amount of each component in the composition of the invention may be varied within wide limits. Thus, substance a) may be present in an amount of 1–50% by weight per unit dose of the composition, and substance b) may be present in an amount of 1–50% by weight. Preferably, in order to obtain a favourable balance of properties, substance a) and substance b) should be present in substantially equal amounts. The acid neutralizing agent c) may be present in an amount of 1–30% by weight per unit dose of the composition, and is preferably present in an amount of at least 5 meq of base per unit dose of the composition in order to provide an adequate acid neutralization.

The composition of the present invention may be used for all the medical purposes involving the administration of antacids. Thus, the present invention further relates to a method of treating or alleviating upper gastrointestinal dyspeptic disorders, comprising administering a therapeutically effective amount of the composition of the invention to a patient in need of such treatment. These disorders include gastrooesophageal reflux, gastritis, gastric or duodenal ulcers, pyrosis and oesophagitis.

It has surprisingly been found that when a low-methoxylated pectin is used as substance a), it may not be necessary to include a buffer substance b) in the composition, yet still be possible to attain a satisfactory acid neutralizing capacity. Thus, in a further aspect, the present invention relates to an antacid composition which comprises a) a low-methoxylated pectin with a degree of methoxylation of less than about 15% or a salt thereof, b) one or more acid neutralizing agents capable of being trapped in the gel formed by the low-methoxylated pectin at an acid pH, at least one of which causes the gel to foam when contacted with an acid, and c) optionally a substance which is capable of acting as a buffer, the composition being formulated so that the low-methoxylated pectin is dissolved before ingestion of the composition and having raftforming properties in a gastric environment.

The salt of the low-methoxylated pectin is for instance an alkali metal salt, such as a sodium or potassium salt.

The low-methoxylated pectin (or pectate) employed in this composition preferably has a degree of methoxylation of less than about 10%, in particular between 0 and 5%.

This composition may otherwise exhibit the properties and be employed for the indications mentioned above.

The invention is further illustrated by the following Examples.

EXAMPLE 1

A chewable tablet according to the invention was prepared from the following ingredients

| Ingredient | Amount in % by weight |
|---|---|
| Pectin* | 21.2 |
| Acid casein | 30.8 |
| Potassium bicarbonate | 14.2 |
| Magnesium subcarbonate | 15.7 |
| Sorbitol | 8.5 |
| Milk powder | 8.5 |
| Peppermint oil | 0.1 |
| Aspartame | 0.1 |
| Magnesium stearate | 0.5 |
| Distilled mono- and diglycerides | 0.5 |
| | 100.0 |

*Low-methoxylated pectin with a degree of methoxylation of 0–5% (used in all Examples).

by mixing the ingredients and compressing the mixture into tablets in a manner known per se. Each tablet contained 5 meq of base and weighed about 1275 mg.

EXAMPLE 2

A chewable tablet according to the invention was prepared from the following ingredients

| Ingredient | Amount in % by weight |
|---|---|
| Pectin | 15.0 |
| Casein | 31.0 |
| Potassium bicarbonate | 14.2 |
| Magnesium subcarbonate | 11.6 |
| Sorbitol | 27.0 |
| Distilled mono- and diglycerides | 0.3 |
| Magnesium stearate | 0.5 |
| Silicon dioxide | 0.2 |
| Flavours | 0.1 |
| Sweetener | 0.1 |
| | 100.0 | by mixing the ingredients and compressing the mixture into tablets in a manner known per se. Each tablet contained 5 meq of base and weighed about 1275 mg.

EXAMPLE 3

A chewable tablet according to the invention was prepared from the following ingredients

| Ingredient | Amount in % by weight |
|---|---|
| Pectin | 15.0 |
| Casein | 15.0 |
| Potassium bicarbonate | 7.2 |
| Magnesium subcarbonate | 18.6 |
| Glycine | 17.4 |
| Sorbitol | 10.0 |
| Lactose | 10.5 |
| Milk powder | 5.0 |
| Mono-, di and triglycerides | 0.5 |
| Magnesium stearate | 0.5 |
| Silicon dioxide | 0.2 |
| Sweetener | 0.1 |
| Flavours | 0.1 |
| | 100.0 | by mixing the ingredients and compressing the mixture into tablets in a manner known per se. Each tablet weighed about 1275 mg.

EXAMPLE 4

A liquid composition of the invention was prepared from the following ingredients

| Ingredient | Amount |
|---|---|
| Pectin | 380 mg |
| Casein | 380 mg |
| Magnesium subcarbonate | 474 mg |
| Potassium bicarbonate | 184 mg |
| Flavours | q.s. |
| Sweetener | q.s. |
| Water | 25 g | by mixing the ingredients in a manner known per se. This mixture may be filled into a suitable container before use.

EXAMPLE 5

Compositions according to the invention (according to Example 1) were tested in vitro in simulated gastric fluid in accordance with the following method:

100 ml of a mixture of simulated gastric fluid (USP XX) and distilled water (4:6), pH about 1.3, were placed on a magnetic stirrer (FRAMO M22/1) operated at 500 rpm. When the pH had stabilized (about 1.25), the antacid sample to be tested was added.

One minute after the addition of the sample, a continuous addition of simulated gastric fluid, pH 1.2, (at a rate of about 2 ml/min. corresponding to about 10 mmoles/hour) was carried out by means of an ISMATEC mini-S 840 pump provided with an ENE 09-tube. The pH was determined by means of a PHM 84 pH meter (Radiometer, Denmark) connected to a BBC, SE 120 recorder.

The composition of the invention was tested with respect to the following parameters: The duration of the latency period before a pH of $\geq 3$ is obtained (this pH was set as the pH at which the antacid effect occurs), the highest pH recorded, variations in the pH range of 3–5, and the duration of the period of time before the reaction mixture reaches a pH of 2, at which pH the experiment is stopped. The composition of the invention was compared with two conventional antacids with respect to these parameters: 1) potassium bicarbonate and magnesium carbonate, and 2) Gaviscon ® (a combination of alginic acid, sodium bicarbonate and aluminum hydroxide, produced by Ferring, Sweden). The results appear from Table 1.

TABLE I

| | Latency period pH $\geq$ 3 (seconds) | Maximum pH | Duration of pH = 3–5 (minutes) | Duration of period before pH = 2 is reached (minutes) |
|---|---|---|---|---|
| Mixture of 340 mg of potassium bicarbonate and 277 mg of magnesium carbonate | 70 | 3.74 | 6.5 | 21 |
| Composition of the invention | 24 | 4.88 | 30.5 | 55 |
| Gaviscon ®, 3000 mg | — | 1.56 | —[1] | —[1] |

[1] As the pH did not reach 3, the duration of the antacid effect could not be recorded.

It appears from the Table that the highest pH (4.88) was recorded for the composition of the present invention. The buffer capacity was also most pronounced for the composition of the invention, pH values of more 2 being recorded for 55 minutes. On the basis of these results, it is concluded that compared with a mixture of alkaline salts and Gaviscon ®, respectively, the product of the invention was found to show the highest acid neutralizing buffer capacity when determined by means of this in vitro method.

EXAMPLE 6

Compositions of the invention were further tested for the effect of incorporating varying amounts of the active ingredients a), b) and c) with respect to the maximum pH obtained and the duration of the acid neutralizing effect. The method used to test these parameters/variables was similar to that described in Example 5, namely the in vitro method using simulated gastric fluid.

The effect of casein on the maximum pH and duration of the acid neutralizing effect appears from Table 2 below. 184 mg of $KHCO_3$ + 480 mg of $MgCO_3$ were used as the base, corresponding to 10 meq of base.

TABLE 2

|  | 10 meq of base (without casein) | 10 meq + 397 mg of casein | 10 meq + 794 mg of casein |
| --- | --- | --- | --- |
| Maximum pH | 5.8 | 5.2 | 5.05 |
| Duration of effect to pH 2.5 | 54 min. | 56 min. | 60 min. |

The effect of pectin on the maximum pH and duration of the antacid effect appears from Table 3 below.

TABLE 3

| Amount of base 5 meq 92 mg of $KHCO_3$ 240 mg of $MgCO_3$ | no pectin added | +546 mg of pectin |
| --- | --- | --- |
| Maximum pH | 4 | 2.0 |
| Duration of effect to pH 2.5 | 16 min. | — |

The effect of the ratio between casein and pectin on the maximum pH, duration of the antacid effect and foaming appears from Table 4 below. The same amount of base, 10 meq (343 mg of $KHCO_3$ + 283 mg of $MgCO_3$), was used in each experiment.

TABLE 4

| Experiment No. | 8 | 1 | 9 | 10 |
| --- | --- | --- | --- | --- |
| Pectin | 238 mg | 378 mg | 630 mg | 382 mg |
| Casein | 1000 mg | 800 mg | 900 mg | 382 mg |
| Maximum pH | 4.5 | 4.9 | 3.5 | 5.7 |
| Foaming | 20 ml | 45 ml | 55 ml | 35 ml |
| Duration of effect to pH 2.5 | 37.5 min. | 36.5 min. | 24 min. | 70 min. |

It appears from Tables 2–4 that the amount of casein incorporated in the composition affects the duration of the acid neutralizing effect expressed as the time period before a pH of 2.5 is obtained so that a larger amount of casein incorporated leads to a longer duration of the effect, while on the contrary, a larger amount of pectin incorporated leads to a lower maximum pH and a shorter duration of the acid neutralizing effect. However, the amount of pectin also affects the degree of foaming obtained, so that, when formulating the composition of the invention, a balance must be reached between the amount of casein and the amount of pectin incorporated in the composition.

EXAMPLE 7

A chewable tablet according to the invention was prepared from the following ingredients:

|  | Alginate |
| --- | --- |
| Casein | 15.0 |
| Alginic acid*) | 15.0 |
| Potassium bicarbonate | 7.2 |
| Magnesium carbonate | 18.6 |
| Glycine | 6.35 |
| Whey powder 15 | 5.0 |
| Xylitol | 30.0 |
| Mono-, di-, triglycerides | 0.5 |
| Magnesium stearate | 0.5 |
| Silicon dioxide | 0.2 |
| Saccharine | 0.15 |
| Citric acid | 1.0 |
| Aroma | 0.5 |
|  | 100.0 |

*)Purchased from Grindsted Products, Denmark (VLVA Sample I; Catalogue No. 2001814)

by mixing the ingredients and compressing the mixture into tablets in a manner known per se. Each tablet weighed about 1275 mg.

This composition was tested as described in Examples 5 and 6 and compared with the composition according to Example 3. The results appear from Table 5 below.

TABLE 5

|  | Alginic acid | Pectin |
| --- | --- | --- |
| Maximum pH | 5.2 | 5.7 |
| Duration of period before pH = 2.0 is reached (minutes) | 84 | 106 |
| Foaming 1 tablet | 6 ml | 25 ml |
| 30 min. 2 tablets | 12 ml | 32 ml |

It appears from Table 5 that alginic acid produces less foaming of the gel than pectin.

EXAMPLE 8

Chewable tablets according to the invention were prepared from the following ingredients:

|  | Protein | Calcium caseinate | No casein | Acid casein |
| --- | --- | --- | --- | --- |
| Pectin | 14.8 | 14.8 | 14.8 | 14.8 |
| Calcium caseinate | — | 30.8 | — | — |
| Acid | — | — | — | 30.8 |
| Soy protein | 30.8 | — | — | — |
| Potassium bicarbonate | 7.2 | 7.2 | 7.2 | 7.2 |
| Magnesium carbonate | 18.6 | 18.6 | 18.6 | 18.6 |
| Tabletting excipients, flavours and sweeteners | 28.6 | 28.6 | 28.6 | 28.6 |
| 1 tablet | 1200 mg | 1200 mg | 830 mg | 1200 mg |
| Foaming | 24 ml | 10 ml | 20 ml | 24 ml | by mixing the ingredients and compressing the mixture into tablets in a manner known per se.

The compositions were tested substantially as described in Examples 5 and 6 for the degree of foaming obtained. The results are shown above. It appears from the table that soy protein compares favourably with acid casein with respect to foaming.

EXAMPLE 9

Clinical Testing of the Composition of the Invention

The composition of Example 1 was tested for its therapeutic effect, possible adverse effects and acceptability in comparison with conventional antacids (Balancid ® [composed of aluminum hydroxide and magnesium carbonate], Novaluzid ® [composed of aluminum hydroxide, magnesium hydroxide and magnesium carbonate], Link ® [composed of aluminum hydroxide and magnesium carbonate] and Titralac [composed of calcium carbonate].

The study was carried out at the out-patients clinic of the medical department of gastro-enterology, Ullevål Hospital, Oslo, Norway, from February to May 1986. 20 patients (12 male and 8 female patients between 23 and 64 years of age) who suffered from upper abdominal dyspeptic symptoms and whose informed consent had been obtained, were included in the study. The average age was 40 years. 15 of the patients used Balancid ® at the time they were included in the study. Patients were excluded from the study if they suffered from a gastroscopically verified peptic ulcer, erosive prepyloric changes, severe gastritis or other organic gastrointestinal diseases that might explain the presence of symptoms, or if they used drugs known to affect the gastrointestinal tract. Thus, all the patients included in the study were diagnosed to suffer from non-ulcer dyspepsia (NUD).

The patients visited the clinic twice, at the beginning of the test treatment and after two weeks of treatment. Three of the patients did not show up at the second consultation which left therapeutic results from 17 patients available. During the test period, the patients daily filled in a dosage form and registered the side effects and adverse reactions experienced. During the two-week period, the composition of Example 1 was taken according to need; however, no more than two tablets were taken at a time. 13 of the patients took the composition of the present invention for the entire period with an average intake of 52 tablets (within a range of 19-100). Four of the patients prematurely stopped taking the composition of the invention: patient No. 3 after 7 days because he had to take Balancid ® as before and therefore saw no reason to continue the treatment with the composition of the invention; patient No. 5 after 8 days because he was free of symptoms; No. 11 because the ingestion of two dosages on the first day lead to nausea and vomiting; and No. 18 after 9 days due to hospitalization with severe vomiting and dehydration (diagnosed as severe gastritis—not ascribable to the ingestion of the composition of the invention).

A final overall evaluation of the composition of the invention was obtained from 17 patients; 11 of the patients were satisfied with the test treatment, 3 considered it to be equal to previous treatment while 3 were dissatisfied (two of the patients due to an insufficient effect and one due to nausea/vomiting). The effect of the composition of the invention is shown in Table 6 with respect to various symptoms registered according to severity and duration.

The results were analyzed statistically using a Student's T-test, p=0.05. Variables with presumed continuous distribution were analyzed using non-parametric tests. For variables with non-continuous distribution, categoric data analysis was used.

TABLE 6

| Symptoms | Improved | Unchanged | Aggravated | |
|---|---|---|---|---|
| Regurgitation | 10 | 6 | 0 | $p < 0.01$ |
| Heartburn | 7 | 6 | 3 | $p = 0.14$ |
| Epigastric pain | 13 | 2 | 1 | $p < 0.01$ |
| Abdominal pain | 5 | 10 | 1 | $p = 0.11$ |
| Nausea | 10 | 6 | 0 | $p < 0.01$ |
| Vomiting | 4 | 12 | 0 | $p = 0.13$ |

The results show that regurgitation, epigastric pain and nausea were significantly reduced ($p < 0.01$) during the two-week test period while heartburn, abdominal pain and vomiting improved, but were not statistically significant. Periods of latency and the duration of the effect appear from Tables 7 and 8.

TABLE 7

| | Period of latency (minutes) | | | |
|---|---|---|---|---|
| | Previous treatment | Composition of the invention | Difference | |
| No. of patients | 12 | 13 | 10 | |
| Mean | 21.6 | 18.8 | −5.9 | |
| Median | 17.5 | 15 | −3.5 | |
| Range | 0.5-60 | 1-60 | (−40)-50 | $p = 0.24$ |

TABLE 8

| | Duration of effect (hours) | | | |
|---|---|---|---|---|
| | Previous treatment | Composition of the invention | Difference | |
| No. of patients | 11 | 13 | 9 | |
| Mean | 5.3 | 7.1 | 0.8 | |
| Median | 3.5 | 5 | 2.5 | |
| Range | 1-24 | 1-24 | (−23)-17 | $p = 0.10$ |

It appears from the Tables that the recordings varied considerably, but the profile of the duration tended to be increased with the composition of the invention than with the conventional antacids used as controls.

It appears from these results that the effect of the composition compares favourably with previous antacid treatment.

EXAMPLE 10

Clinical Testing of the Composition of the Invention

The composition of Example 3 was radiolabelled with indium-113m and the gastric distribution and residence time of the composition was then measured in six healthy subjects using the technique of gamma scintigraphy, and the effect of the formulation on the gastric emptying of a test meal was measured.

Four healthy male and 2 healthy female subjects, age range 18-25 years, participated in the trial. Exclusion criteria included weight outside the range of ±10% group mean weight, consumption of medications which could influence the results of the study, a history of gastrointestinal disorders, excessive tobacco or alcohol consumption or participation in a similar study within the previous 12 months. Female subjects who had not menstruated within the previous 28 days were also excluded. Written informed consent was obtained from the subjects prior to entry into the trial.

The subjects were fasted overnight and on the morning of the study given a radiolabelled scrambled egg breakfast composed of 2 eggs (60 g) radiolabelled with 1 MBq technetium-99 m sulphur colloid added to the egg prior to cooking, 30 ml of milk,
25 g of butter,
2 slices of toast,
200 ml of unsweetened orange juice.
Total calorific value 1693 kJ.

The scrambled eggs were labelled by addition of technetium-99 m sulphur colloid to the ingredients before cooking.

Thirty minutes later, the subjects were given two radiolabelled crushed tablet in 20 ml of water or a placebo. The tablets had been radiolabelled by adding 3 MBq indium-113 m in 1 ml of 0.04M hydrochloric acid to 2 crushed tablets of the composition of Example 3, and this was stirred until a uniform paste was formed. This was added to 125 ml of simulated gastric juice (USP formulation) at 37° C. The mixture was stirred to form a suspension in the acid. 2 ml samples of the mixture were removed at intervals and centrifuged at 2500 rpm. The pellet was washed by resuspending it in distilled water and by recentrifugation. Samples of the pectin, washings and supernatant were counted to assess the tenacity of the radiolabel for the pectin.

A cross-over study was performed, separated by a one week interval. Anatomical reference markers were made by drying small quantities of technetium-99m onto $0.5 \times 0.5$ cm$^2$ pieces of filter paper and covering with waterproof tape. The markers were taped on the subjects' skin anteriorly and posteriorly, opposite the stomach, to act as a reference point for alignment of images.

Anterior and posterior images of 30 seconds' duration were recorded at 15 minutes' intervals until the stomach was empty (approximately 5 hours). The technetium and indium images were recorded simultaneously but stored separately in the computer for subsequent analysis.

Each image was analyzed by creating three regions of interest, one around the whole stomach, the second around the top half of the stomach and the third to assess background activity. The count rates from the regions of interest were corrected for background and decay. The technetium count rates were also corrected for the overlap of the indium energy into the technetium channel. The geometric mean of the activity in the regions of interest in the anterior and posterior images were calculated to correct for attenuation.

More than 86% of the indium-113 m was found to be associated with the pectin phase after two hours of incubation with simulated gastric juice at 37° C. in vitro. This established the suitability of the label to enable the behavior of this formulation to be followed by gamma scintigraphy.

The composition of the invention emptied significantly later than the test meal and more than 50% of the dose remained in the fundus for 3 hours. The time for half the formulation and food to leave the stomach (T$_{50}$) for each subject is shown in Table 9 and the mean T$_{50}$s±sd are 4.13±0.69 hours and 2.17±0.15 hours, respectively. The composition of the invention was not found to have a significant effect on the gastric emptying of the test meal, with T$_{50}$s of 2.17±0.15 hours and 1.7±0.32 hours for drug and placebo, respectively.

TABLE 9

| | Time (hours) taken to half empty stomach | | |
|---|---|---|---|
| Subject | Composition | Food + composition | Food + placebo |
| 1 | 4.4 | 2.2 | 1.4 |

TABLE 9-continued

| | Time (hours) taken to half empty stomach | | |
|---|---|---|---|
| Subject | Composition | Food + composition | Food + placebo |
| 2 | 4.1 | 2.1 | 1.4 |
| 3 | 4.36 | 2.3 | 1.6 |
| 4 | 4.6 | 2.25 | 2.3 |
| 5 | 4.25 | 2.25 | 2.0 |
| 6 | 2.8 | 1.9 | 1.7 |
| Mean ± s.d. | 4.13 ± 0.69 | 2.17 ± 0.15 | 1.7 ± 0.32 |

EXAMPLE 11

An effervescent tablet according to the invention was prepared from the following ingredients:

| | |
|---|---|
| Citric acid | 800 mg |
| Potassium bicarbonate | 500 mg |
| Sodium bicarbonate | 500 mg |
| Magnesium carbonate | 480 mg |
| Pectin | 380 mg |
| Casein | 380 mg |
| Tabletting excipients, flavour, colour and sweetener | 960 mg |
| | 4000 mg |

The amount of foaming after 30 minutes was 35 ml when the composition was tested as described in Examples 5 and 6.

REFERENCES

1. H. A. May, C. G. Wilson, J. G. Hardy, *Int. J. Pharm.* 19, 1984, 169–176.
2. N. Washington, C. Washington, C. G. Wilson, *Int. J. Pharm.* 1987, in press.
3. B. Flourie, N. Vidon, J. A. Chayvialle et al., *Am. J. Clin. Nutr.* 42, 1985, 495–503.
4. M. Feldman, H. J. Smith, T. R. Simon, *Gastroenterology* 87, 1984, 895–902.
5. L. S. Malmud, N. D. Charkes, J. Littlefield et al., *J. Nucl. Med.* 20, 1979, 1023–1028.
6. L. S. Knight, A. H. Maurer, L. A. Anmar et al., *J. Nucl. Med.* 27, 1986, 1011–1012.
7. B. Flourie, N. Vidon, C. Florent, J. J. Bernier, *Gut* 25, 1984, 936–941.
8. S. Holt, R. C. Heading, D. C. Carter et al., *Lancet i*, 1981, 636–639.
9. A. R. Leeds, D. N. Ralphs, F. Ebied et al., *Lancet i*, 1981, 1075–1078.
10. D. N. Ralphs, O. Lawaetz, N. J. G. Brown, *Gut* 19, 1978, 986-7A abstract.

We claim:

1. An antacid composition which comprises
   i) a low-methoxylated pectin having a degree of methoxylation of not more than 15%, or an alkali salt metal or amidated derivative thereof, which is capable of forming a gel structure at an acid pH;
   ii) one or more acid neutralizing agents capable of being trapped in said gel structure formed by said low-methoxylated pectin at an acid pH, at least one of said acid neutralizing agents which cause said gel to foam when contacted with an acid and which is selected from the group consisting of alkali metal and alkaline earth metal salt, an aluminum salt, an ammonium or a bismuth salt, said salt being a carbonate, bicarbonate, subcarbonate or a mixture thereof; and iii) optionally, a substance which is capable of acting as a buffer and capable of being captured in said gel structure formed by said low-methoxylated pectin at an acid pH, said substance iii) being selected from the group consisting of proteinaceous substances, sodium, calcium, magnesium, ammonium, aluminum and potassium phosphates; casein or caseinates; milk powder; gelatin and amino acids, or a salt thereof;

said composition having raft-forming properties in a gastric environment.

2. The composition according to claim 1, wherein said salt of said low-methoxylated pectin is an alkali metal salt selected from sodium and potassium salts.

3. The composition according to claim 1, wherein said low-methoxylated pectin or salt or amidated derivative thereof has a degree of methoxylation of less than 10%.

4. The composition according to claim 1, wherein at least one of said acid neutralizing agents ii) is present in combination with a member selected from the group consisting of sodium, potassium, magnesium, calcium and aluminum hydroxides; and sodium, potassium, magnesium, calcium and aluminum oxides.

5. The composition according to claim 1, wherein at least one of said acid neutralizing agents ii) is selected from the group consisting of sodium and potassium bicarbonates and carbonates.

6. The composition according to claim 1, wherein at least one of said acid neutralizing agents ii) is selected from the group consisting of ammonium carbonate and ammonium bicarbonate.

7. The composition according to claim 1, wherein at least one of said acid neutralizing agents ii) is bismuth carbonate.

8. The composition according to claim 1, wherein at least one of said acid neutralizing agents ii) are magnesium subcarbonate in combination with potassium bicarbonate.

9. The composition according to claim 3, wherein said low-methoxylated pectin or salt or amidated derivative thereof has a degree of methoxylation of not more than 5%.

10. The composition according to claim 1, which is in the form of a chewable tablet.

11. The composition according to claim 1, which is formulated as a liquid.

12. The composition according to claim 1, wherein said low-methoxylated pectin is present in an amount of 1-50% by weight per unit dose of said composition.

13. The composition according to claim 1, wherein said substance iii) is present in an amount of up to 50% by weight per unit dose of said composition.

14. The composition according to claim 1, wherein said low-methoxylated pectin and said substance iii) are present in substantially equal amounts.

15. The composition according to claim 1, wherein said acid neutralizing agent ii) is present in an amount of 1-30% by weight per unit dose of said composition.

16. The composition according to claim 1, wherein said acid neutralizing agent ii) is present in an amount of at least 5 meq of base per unit dose of said composition.

17. A method of treating or alleviating upper gastrointestinal dyspeptic disorders, comprising administering to a patient in need thereof a therapeutically effective amount of a composition according to claim 1.

18. The method according to claim 17, wherein said dyspeptic disorder is selected from gastroesophageal reflux, gastritis, gastric or duodenal ulcers, pyrosis and oesophagitis.

19. The composition according to claim 1, wherein said alkali metal salt is selected from the group consisting of sodium and potassium salts, and said alkaline earth metal salt is selected from the group consisting of magnesium and calcium salts.

20. The composition according to claim 1 wherein said proteinaceous substance is selected from the group consisting of vegetable proteins and soy protein isolate.

21. The composition according to claim 1 wherein said caseinates are selected from the group consisting of sodium, potassium and ammonium caseinates.

22. The composition according to claim 1 wherein said amino acid is glycine.

23. The composition according to claim 1 wherein at least one of said acid neutralizing agents ii) are magnesium subcarbonate in combination with potassium bicarbonate and said low-methoxylated pectin or salt or amidated derivative thereof has a degree of methoxylation of not more than 5%.

* * * * *

UNITED STATES PATENT AND TRADEMARK OFFICE
CERTIFICATE OF CORRECTION

PATENT NO. : 5,068,109

DATED : November 26, 1991

INVENTOR(S) : Foldager et al

It is certified that error appears in the above-identified patent and that said Letters Patent is hereby corrected as shown below:

On the Title page, item [75],
  Inventors: Please change to read as follows:

-- Jorgen Foldager, Snekkersten; Helle Toftkjaer, Naerum; Kim Kjornaes, Vaerlose, all of Denmark--

Other Publications:

Line 9, change "Mulmud et al." to --Malmud et al.--
  Line 16, change "The Lancet i; 1981" to --The Lancet, March 24, 1979--

Claim 1

Line 3, change "salt" to --metal--
  Line 4, change "metal" to --salt--

Signed and Sealed this

Twenty-seventh Day of April, 1993

*Attest:*

MICHAEL K. KIRK

*Attesting Officer*          Acting Commissioner of Patents and Trademarks